United States Patent
Schmidt et al.

(10) Patent No.: US 6,169,778 B1
(45) Date of Patent: Jan. 2, 2001

(54) COMPUTED TOMOGRAPHY DEVICE

(75) Inventors: Martin Schmidt, Emskirchen; Otto Sembritzki, Wachenroth, both of (DE)

(73) Assignee: Siemens Aktiengesellschaft, Munich (DE)

(*) Notice: Under 35 U.S.C. 154(b), the term of this patent shall be extended for 0 days.

(21) Appl. No.: 09/273,595

(22) Filed: Mar. 22, 1999

(30) Foreign Application Priority Data

Mar. 24, 1998 (DE) .............................. 198 12 973

(51) Int. Cl.$^7$ .................................................. A61B 06/03
(52) U.S. Cl. .................................................. 378/15; 378/4
(58) Field of Search .............................. 378/4, 8, 15, 19, 378/20, 114

(56) References Cited

U.S. PATENT DOCUMENTS 5,175,754 * 12/1992 Casey et al. .............................. 378/4
5,636,255    6/1997 Ellis .
5,841,830 * 11/1998 Barni et al. .............................. 378/15

* cited by examiner

Primary Examiner—David P. Porta
(74) Attorney, Agent, or Firm—Schiff Hardin & Waite

(57) ABSTRACT

A computed tomography (CT) device has a stationary frame and a rotor, carrying an X-ray source and a radiation detector, which is rotatably mounted at the frame. A number of marks are provided at the rotor at known angular intervals, these marks being scanned by a sensor, which is attached at the frame and which emits an output signal given the passing of a mark. The number of marks is significantly lower than the number of projections that are picked up in each rotation of the rotor. A computing unit determines the projection angles pertaining to the individual projections by interpolation from the output signals of the sensor.

18 Claims, 2 Drawing Sheets

COMPUTED TOMOGRAPHY DEVICE

BACKGROUND OF THE INVENTION

1. Field of the Invention

The invention relates to a computed tomography (CT) of the type having a stationary frame, a rotary unit mounted carrying an X-ray source which emits an X-ray beam, and a detector system for the X-rays wherein an examined subject is irradiated by the X-ray beam, and the detector system emits a dataset corresponding to the intensity of the received radiation at a number of projection angles in each rotation of the rotary unit; and wherein an electronic computing unit reconstructs an image of at least a part of the region of the subject which is irradiated with the X-ray beam from the datasets, in consideration of the respective projection angles.

2. Description of the Prior Art

In the above type of CT device, a slotted disk is provided for determining the projection angles, this disk being scanned by an optical sensor and having a number of slots equal at least to the number of projection angles. The technical realization of such a slotted disk is problematic, given the necessary accuracy or precision of at least $\frac{1}{100}$ mm. Furthermore, due to its large diameter, the slotted disk must be composed of a number of segments, whose positioning is very difficult, particularly at the joints. In addition, contamination in the region of the very narrow slots of the slotted disk can result in functional errors.

SUMMARY OF THE INVENTION

An object of the present invention is to provide a CT device of the initially-described type wherein the determination of the projection angles appertaining to the individual projections can occur simply and cost-effectively.

The above object is achieved in accordance with the principles of the present invention in a computed tomography (CT) device having a stationary frame, and a rotary unit carrying an X-ray source and a radiation detector, which is rotatably mounted at the frame. The rotary unit has a number of marks thereon respectively disposed at known angular intervals, these marks being scanned by a sensor which is attached to the frame, and which emits an output signal as each mark passes the sensor. The number of marks is significantly lower than the number of projection angles which are employed for irradiating the examination subject during each rotation of the rotary unit. Datasets from the radiation detector for each of the projection angles, and signals indicating the passage of the respective marks passed the sensor, are supplied to a computing unit, from which the respective projection angles associated with the datasets are determined by interpolation from the output signals of the sensor.

In the case of the Invention, a significant simplification is achieved because a relatively low number of marks is required compared to the number of projection angles, thus the marks need not be produced with extreme precision, since it suffices for the subsequent detection of the projection angles by interpolation if the angular distances of the marks from each other are known. Simulations have shown that, in the case of an inventive CT device, it is possible to determine the projection angles with such a high degree of accuracy that there are no discernible adverse effects on the image quality compared to a CT device according to the prior art, which operates with a slotted disk. It is advantageous, though not imperative, to arrange the marks at substantially equal intervals. The precision of the angle calculation increases with the number of marks, up to an upper limit of twelve marks. The delay after which the angles can be calculated decreases with as the number of marks increases.

A particularly exact detection of the projection angles is possible according to an embodiment of the invention wherein the detector system is prompted to emit the datasets that respectively correspond to the projections by a first clock signal, and wherein the detection of the respective projection angles appertaining to the projections occurs on the basis of a second clock signal, which is synchronized with the first clock signal. In certain circumstances it is possible for the first and the second clock signals to be identical.

A particularly high degree of precision in identifying the angle of projection is possible if the detection of the projection angle occurs with a resolution of at least 15,000 angular increments per rotation of the rotary unit.

It enhances the precision of the detection of the projection angle if the interpolation occurs according to a second order polynomial.

According to an embodiment of the Invention, at least six marks, preferably twelve, are provided. It is clear that, as a result of their low number, the marks are constructed so as to be relatively large, and are consequently robust, and thus less susceptible to disturbances as well as simpler and more economic to produce. In addition, significantly larger sensors can be employed.

According to a preferred inventive embodiment, the sensor operates on a magnetic, inductive, optical or capacitive basis, and that the marks are composed of a corresponding material. The marks can be of a virtually arbitrarily thickness without compromising the operability, while, in the case of the known slotted disks, the thickness of the slotted disk may not exceed a few tenths of a millimeter, due to the necessity of making the slots with such a small width.

DESCRIPTION OF THE PREFERRED EMBODIMENTS

Figure 1:
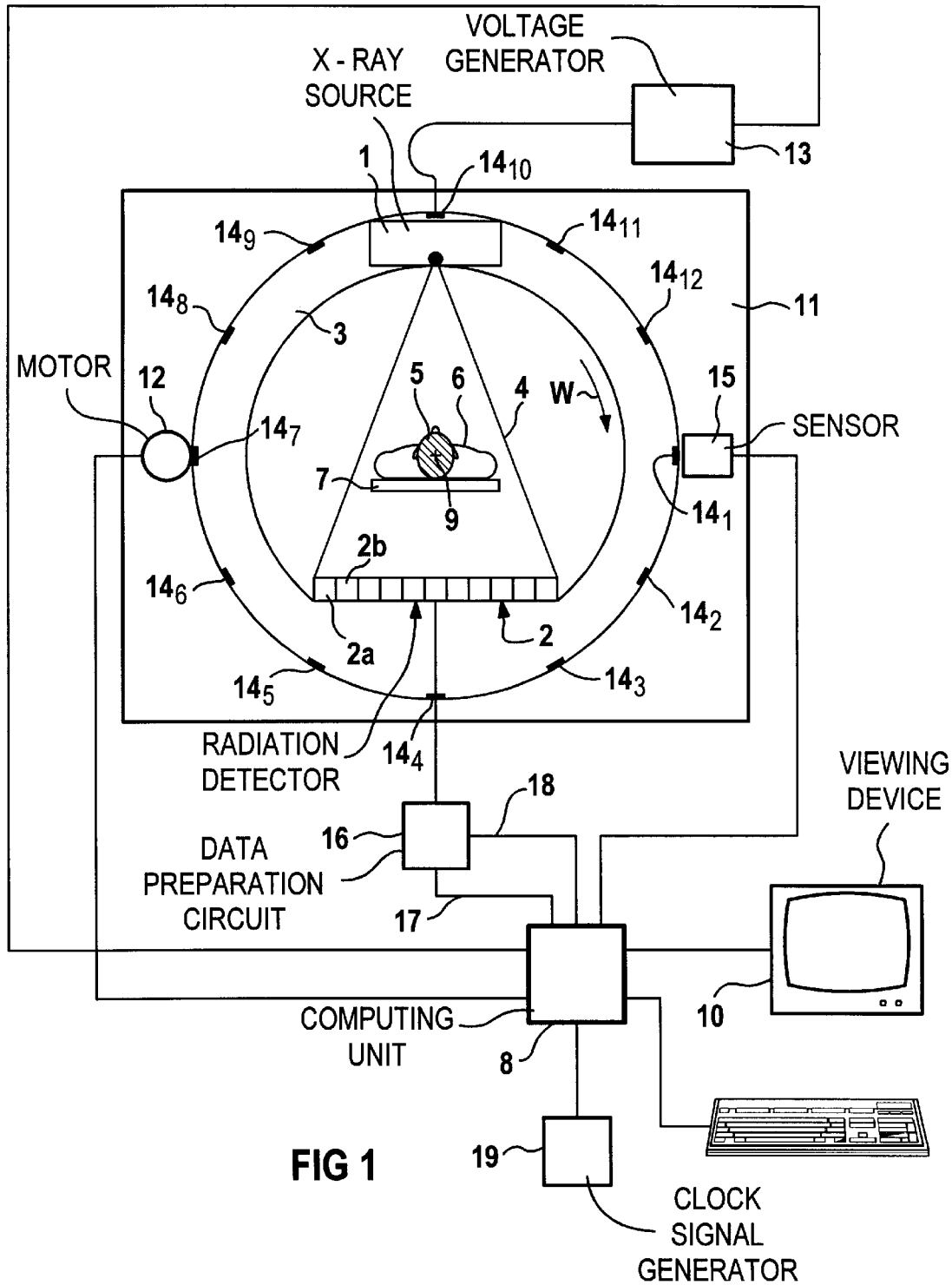
FIG. 1 is a schematic block diagram of an inventive CT device.

The inventive CT device illustrated in FIG. 1 has an X-ray tube 1, which, together with a detector system 2, constitutes a measurement system. The detector system 2 is formed by a series of individual detectors 2a, 2b, etc. The X-ray tube is fixedly connected to the detector system 2 via an annular rotor 3 and emits a fan-shaped X-ray beam 4, which passes through a slice 5 of an examined patient 6. The patient 6 lies on a patient bed 7. The number of individual detectors 2a, 2b, etc. of the detector system 2 is selected according to the desired image resolution. Each individual detector 2a, 2b, etc. emits an electrical signal which corresponds to the intensity of the X-rays incident thereon.

The individual detectors 2a, 2b, etc. of the detector system 2 are connected to an electronic computing unit 8, which computes the X-ray attenuation values of volume elements of the slice 5 from the output signals of the individual detectors 2a, 2b, etc. during the rotation of the measurement system around an axis of rotation 9, which preferably extends parallel to the longitudinal direction of the patient bed 7. Using the X-ray attenuation values, the computing unit 8 calculates a sectional image of the examined slice 5, which can be reproduced on a viewing device 10, a defined gray value or color value in the display of the sectional image corresponding to a defined X-ray attenuation value. A number of projections, e.g. m=1000, are picked up during the rotation of the measurement system around the axis of rotation 9; i.e., in periodic time intervals which correspond to the ratio T/m, wherein T is the rotation time of the rotor 3 (i.e. the time required by the rotor 3 to complete a rotation of 360°) and wherein m is the number of projections. The duration of these intervals is equal to the integration time of the detector system 2. The output signals of the individual detectors 2a, 2b, etc. of the detector system 2 are acquired for the corresponding projection angles w(t) and are supplied to the computing unit 8. In this manner, given 512 individual detectors in the detector system 2, for example, in each rotation of the rotor 3, m projections can be generated for every 512 output signals, which are employed as the basis for the calculation of the X-ray attenuation values of the volume elements of a slice 7. For clarity, the exemplary embodiment does not depict all 512 individual detectors, but only a few.

The rotation of the rotor 3, which is mounted in a frame 11, is effected by a motor 12 which is attached to the frame 11, the motor 12 is actuated in the required manner by an electronic computing unit 8 acting as a control unit. The X-ray tube 1 is supplied with the required currents and voltages by a voltage generator 13, which is likewise controlled in the necessary manner by the electronic computing unit 8 as a control unit. A separate control unit can also be provided for the control of the X-ray tube 1, and possibly other components of the CT device as well.

In order to be able to calculate a correct sectional image from the registered projections, in addition to the sets of output signals (datasets) of the detector system 2 that pertain to the respective projections, the computing unit 8 also requires "knowledge" of the angle w(t) of the respective projection at which a given dataset was generated.

In order to be able to detect the projection angles w(t), in the inventive CT device twelve marks $14_1$ to $14_{12}$ are arranged along the outer perimeter of the rotor 3, these marks being respectively disposed at known angular distances from one another, namely approximately 30°. A sensor 15 is attached to the frame 11, by which the marks $14_1$ to $14_{12}$ pass during the rotation of the rotor 3. Each time one of the marks $14_1$ to $14_{12}$ passes the sensor 15, the sensor 15 emits a pulsed output signal for the duration the mark is in the field of view of the sensor 15. The mark $14_1$, which designates the 0° position (FIG. 1), is fashioned so as to be wider that the other marks $14_2$ to $14_{12}$, so that the 0° position is characterized by an extended pulse duration of the output signal of the sensor 15.

During the preparation for a scan, the computing unit 8 actuates the motor 12 so that the rotor 3 rotates with an approximately constant angular velocity.

In addition, at periodically recurring times during the scanning of the slice 5, as already mentioned, the computing unit 8 also reads the datasets, via a data line 17, corresponding to the individual projections from the data preparation circuit 16 that is connected to the detector system 2. To this end, a corresponding first clock signal is fed to the data preparation circuit 16 via a trigger line 18, this signal being synchronized with the clock signal of a clock generator 19 that is connected to the computing unit 8.

To determine the projection angles w(t) pertaining to the individual projections, the computing unit 8 first determines the times at which the consecutive pulsed output signals of the sensor 15 arise, which are emitted when the marks $14_1$ to $14_{12}$ pass the sensor 15. The determination of these times occurs on the basis of a second clock signal, which is likewise derived from the signal of the clock generator 19 and which thus is synchronized with the first clock pulse. The frequency of the second clock signal must be selected such that the time interval between consecutive pulsed output signals of the sensor 15 can be determined with a precision which corresponds to $1/15,000$ of the rotation period of the rotor 3.

The projection angles w(t) pertaining to the individual projections are determined by interpolation from the times $t_1$ to $t_{12}$, which are determined as described above.

In the case of the present exemplary embodiment, the interpolation proceeds on the basis of a second-order polynomial according to the following formula:

$$w(t) = \frac{(t-t_{\parallel})-(t-t_{\Sigma})}{(t_{\cap}-t_{\parallel})(t_{\cap}-t_{\Sigma})} \cdot w_{\cap} + \frac{(t-t_{\cap})-(t-t_{\Sigma})}{(t_{\parallel}-t_{\cap})(t_{\parallel}-t_{\Sigma})} \cdot w_{\parallel} + \frac{(t-t_{\cap})-(t-t_{\parallel})}{(t_{\Sigma}-t_{\cap})(t_{\Sigma}-t_{\parallel})} \cdot w_{\Sigma}$$

with w(t) being the projection angle pertaining to the projection picked up at the time t, and $w_n$ to $w_{n+2}$ (n=1,4,7,10) being the angular distances of the three marks which pass the sensor 15 at the times $t_1$ to $t_3$, with $t_1 \le t \le t_3$. Thus, all the projections picked up between the angles $w_1=0$, $w_2=30°$ and $w_3=60°$, i.e. during the projections picked up between $t_1=0$ and $t_3$, are determined by interpolation according to the above equation, with n=1, after the time $t_3$ has been attained, i.e. the angle $w_3$ has been covered. For the angles from 60° to 120°, 120° to 180°, etc. the same method is followed, with n=4, n=7 and n=10.

Figure 2:
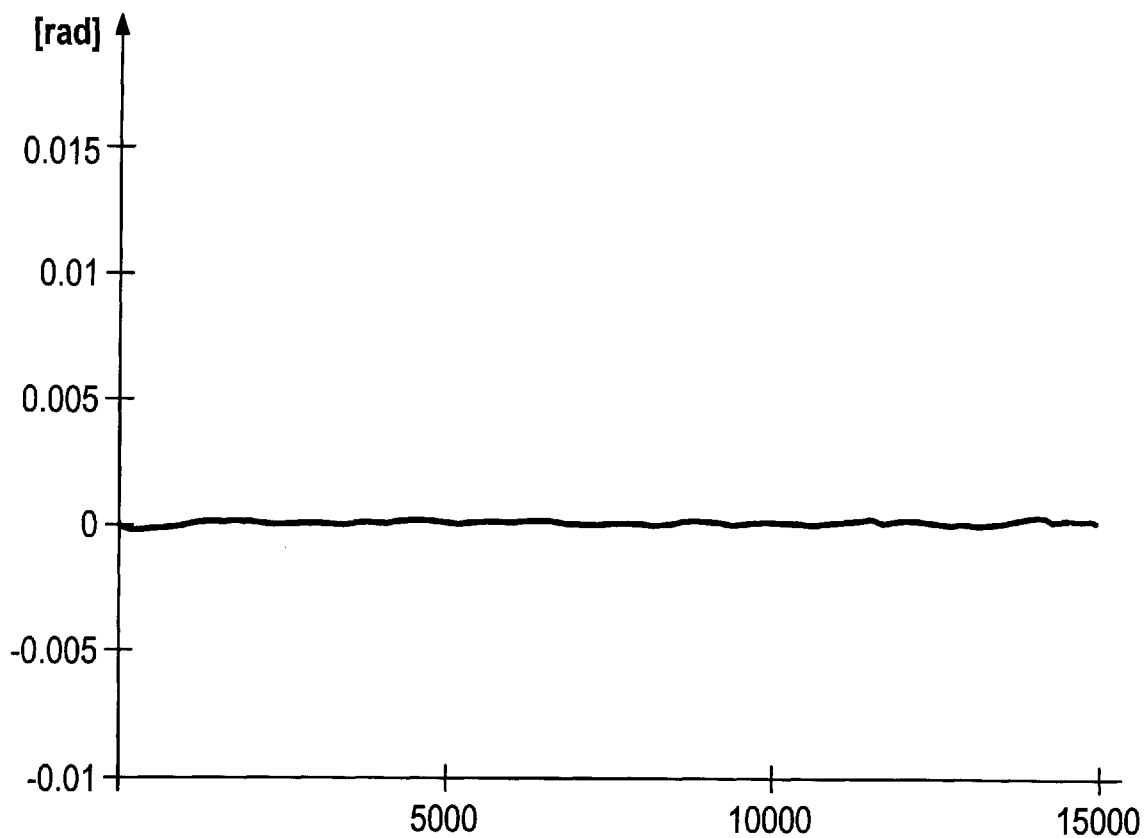
FIG. 2 is a diagram illustrating the error arising in the detection of the projection angles in the device according to FIG. 1.

The determination of the projection angles w(t) thus is possible with a very high precision. As shown in FIG. 2, in the case where the detection of the projection angles occurs with a resolution of at least 15,000 angular increments per rotation of the rotor 3, angular deviations derive which lie well under 0.005 radians. These low deviations are based on the fact that the angular velocity of the rotor 3 fluctuates only slightly, due to the typically large inertial mass of the rotor 3 with the attached components. The described interpolation method is also responsible for the high precision. In addition, the high precision is achieved because the first clock signal, which is necessary for the readout of the datasets, is synchronized with the second clock signal, which is necessary for the determination of the times $t_1$ to $t_{12}$.

Alternatively, the determination of the projection angles w(t) according to the above equation can occur with n=1, 2, 3, etc., up to 10, for example, whereby, after the attainment of the angle $w_3$ and the time $t_3$, the projection angles between the angles $w_1=0$ and $w_2=30$ are calculated with n=1; after the attainment of the angle $w_4$ and the time $t_4$, the projection angles between the angles $w_2=30$ and $w_3=60°778$ are calculated with n=2; and so on.

The sensor 15 can be a sensor which operates on a magnetic, inductive, capacitive or optical basis, the marks $14_1$ to $14_{12}$ being fashioned in the first instance as magnets, preferably permanent magnets, in the second and third instances as metallic elements, and in the fourth instance as optically non-transparent bodies.

Departing from the described exemplary embodiment, the clock generator 19 can alternatively be a part of the computing unit 8. Furthermore, the data preparation circuit 19 can be integrated into the detector system 2.

Furthermore, departing from the exemplary embodiment, the marks $14_1$ to $14_{12}$ can be attached to the frame 11, with sensor 15 attached on the rotor 3. This version, however, necessitates data transmission from the rotating sensor 15 to the stationary computing unit 8.

The Invention is described above in the example of a CT device of the third generation, however, it can also be used in CT devices of other generations.

Unlike the exemplary embodiment, it is also possible to have the rotor 3 rotate continuously, while displacing the patient bed 7 with the patient 6 in the direction of its longitudinal axis (spiral CT), so that a volume of the patient 6 is scanned, rather than a single slice. In this case as well, the detection of the projections that are picked up during the individual rotations of the rotor 3 can occur as described.

The invention is described above in the example of a medical application; however, it can also be used outside of the field medicine; for example, for purposes of material investigation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:

a stationary frame;

a rotary unit rotatably mounted to said stationary frame, said rotary unit comprising a rotatable rotor and an X-ray source mounted on said rotor, said X-ray source emitting an X-ray beam and irradiating an examination subject from a plurality of different projection angles during rotation of said rotary unit, and said radiation detector producing a dataset for each of said projection angles;

a plurality of marks on said rotor at predetermined angular distances from each other, said plurality of marks being significantly less than said plurality of projection angles;

a sensor disposed on said frame having a field of view through which said marks pass as said rotary unit rotates, and said sensor emitting a sensor output signal upon a passage of each mark through said field of view; and a computing unit supplied with said datasets and said sensor output signals, said computing unit determining the respective projection angles associated with the datasets by interpolation from said sensor output signals, and producing image data from said datasets and said projection angles.

2. A computed tomography device as claimed in claim 1 further comprising a clock signal source which emits a first clock signal and a second clock signal synchronized with said first clock signal, and wherein said radiation detector is connected to said clock signal source to receive said first clock signal and wherein said radiation detector emits the respective datasets dependent on said first clock signal, and wherein said second clock signal is supplied to said computing unit and said computing unit identifies said projection angles dependent on said second clock signal.

3. A computed tomography device as claimed in claim 1 wherein said computing unit identifies said projection angles with a resolution of at least 1500 angular increments per rotation of said rotary unit.

4. A computed tomography device as claimed in claim 1 wherein said computing unit employs a second order polynomial for making said interpolation.

5. A computed tomography device as claimed in claim 1 wherein said plurality of marks comprises at least six marks.

6. A computed tomography device as claimed in claim 1 wherein said marks are comprised of magnetic material and wherein said sensor comprises a magnetic sensor.

7. A computed tomography device as claimed in claim 1 wherein said sensor comprises an inductive sensor having an inductance, and wherein said marks are comprised of material influencing said inductance of said inductive sensor.

8. A computed tomography device as claimed in claim 1 wherein said sensor comprises a capacitive sensor having a capacitance, and wherein said marks comprise material influencing said capacitance of said capacitive sensor.

9. A computed tomography device as claimed in claim 1 wherein said marks comprise optically visible material, and wherein said sensor comprises an optical sensor.

10. A computed tomography apparatus comprising:

a stationary frame;

a radiation detector;

a rotary unit rotatably mounted to said stationary frame, said rotary unit comprising a rotatable rotor and an X-ray source mounted on said rotor, said X-ray source emitting an X-ray beam and irradiating an examination subject from a plurality of different projection angles during rotation of said rotary unit, and said radiation detector producing a dataset for each of said projection angles;

a plurality of marks on said frame at predetermined angular distances from each other, said plurality of marks being significantly less than said plurality of projection angles;

a sensor disposed on said rotor having a field of view through which said marks pass as said rotary unit rotates, and said sensor emitting a sensor output signal upon a passage of each mark through said field of view; and a computing unit supplied with said datasets and said sensor output signals, said computing unit determining the respective projection angles associated with the datasets by interpolation from said sensor output signals, and producing image data from said datasets and said projection angles.

11. A computed tomography device as claimed in claim 10 further comprising a clock signal source which emits a first clock signal and a second clock signal synchronized with said first clock signal, and wherein said radiation detector is connected to said clock signal source to receive said first clock signal and wherein said radiation detector emits the respective datasets dependent on said first clock signal, and wherein said second clock signal is supplied to said computing unit and said computing unit identifies said projection angles dependent on said second clock signal.

12. A computed tomography device as claimed in claim 10 wherein said computing unit identifies said projection angles with a resolution of at least 1500 angular increments per rotation of said rotary unit.

13. A computed tomography device as claimed in claim 10 wherein said computing unit employs a second order polynomial for making said interpolation.

14. A computed tomography device as claimed in claim 10 wherein said plurality of marks comprises at least six marks.

15. A computed tomography device as claimed in claim 10 wherein said marks are comprised of magnetic material and wherein said sensor comprises a magnetic sensor.

16. A computed tomography device as claimed in claim 10 wherein said sensor comprises an inductive sensor having an inductance, and wherein said marks are comprised of material influencing said inductance of said inductive sensor.

17. A computed tomography device as claimed in claim 10 wherein said sensor comprises a capacitive sensor having a capacitance, and wherein said marks comprise material influencing said capacitance of said capacitive sensor.

18. A computed tomography device as claimed in claim 10 wherein said marks comprise optically visible material, and wherein said sensor comprises an optical sensor.

* * * * *